(12) United States Patent
Raslambekov (10) Patent No.: US 11,197,742 B2
(45) Date of Patent: *Dec. 14, 2021

(54) INTRA-ORAL DEVICE

(71) Applicant: 3D MED AG, Zug (CH)

(72) Inventor: Islam Khasanovich Raslambekov, Moscow (RU)

(73) Assignee: 3D MED AG, St. Moritz (CH)

( * ) Notice: Subject to any disclaimer, the term of this patent is extended or adjusted under 35 U.S.C. 154(b) by 431 days.

This patent is subject to a terminal disclaimer.

(21) Appl. No.: 16/240,964

(22) Filed: Jan. 7, 2019

(65) Prior Publication Data

US 2020/0069397 A1    Mar. 5, 2020

Related U.S. Application Data (63) Continuation of application No. 16/119,068, filed on Aug. 31, 2018, now Pat. No. 10,251,729.

(51) Int. Cl.
*A61C 7/36*     (2006.01)
*A61C 7/10*     (2006.01)
(Continued)

(52) U.S. Cl.
CPC .................. *A61C 7/36* (2013.01); *A61C 7/08* (2013.01); *A61C 7/10* (2013.01); *A61F 5/566* (2013.01); *A63B 71/085* (2013.01)

(58) Field of Classification Search
CPC ....... A61C 7/36; A61C 7/08–10; A61F 5/566; A63B 71/085
See application file for complete search history.

(56) References Cited

U.S. PATENT DOCUMENTS 4,239,487 A  *  12/1980  Murdock ................. A61C 7/00
                                                                         433/7
4,416,626 A  *  11/1983  Bellavia .................... A61C 7/00
                                                                         433/7
(Continued)

FOREIGN PATENT DOCUMENTS

DE          29915769 U1     3/2000
WO          98058596 A1     12/1998
(Continued)

OTHER PUBLICATIONS

Partial European Search Report dated Feb. 7, 2019 in respect of the European patent application No. 18192132.1.
(Continued)

*Primary Examiner* — Jacqueline T Johanas
*Assistant Examiner* — Shannel Nicole Belk
(74) *Attorney, Agent, or Firm* — BCF LLP (57) ABSTRACT

An intra-oral device comprising upper and lower jaw applicators, the upper jaw applicator comprising upper left and upper right components, and the lower jaw applicator comprising lower left and lower right components; a transverse adjustment mechanism for simultaneously adjusting a distance between the upper left and upper right components, and the lower left and lower right components wherein the transverse adjustment mechanism comprises: a threaded rod having one end portion engageable with the upper left and lower left components, and another end portion engageable with the upper right and the lower right components.

17 Claims, 8 Drawing Sheets

(51) Int. Cl.
*A61C 7/08* (2006.01)
*A61F 5/56* (2006.01)
*A63B 71/08* (2006.01)

(56) References Cited

U.S. PATENT DOCUMENTS

| | | | |
|---|---|---|---|
| 4,433,956 A * | 2/1984 | Witzig | A61C 7/10 433/7 |
| 4,708,646 A | 11/1987 | Jasper | |
| 4,802,849 A * | 2/1989 | Collins, Jr. | A61C 7/00 433/18 |
| 5,570,704 A | 11/1996 | Buzzard et al. | |
| 5,683,244 A | 11/1997 | Truax | |
| 5,700,263 A | 12/1997 | Schendel | |
| 5,885,283 A | 3/1999 | Gittleman | |
| 5,975,893 A | 11/1999 | Chishti et al. | |
| 6,099,304 A | 8/2000 | Carter et al. | |
| 6,183,248 B1 | 2/2001 | Chishti et al. | |
| 6,227,850 B1 | 5/2001 | Chishti et al. | |
| 6,309,215 B1 | 10/2001 | Phan et al. | |
| 6,318,994 B1 | 11/2001 | Chishti et al. | |
| 6,334,853 B1 | 1/2002 | Kopelman et al. | |
| 6,386,878 B1 | 5/2002 | Pavlovskaia et al. | |
| 6,398,548 B1 | 6/2002 | Muhammad et al. | |
| 6,463,344 B1 | 10/2002 | Pavloskaia et al. | |
| 6,471,511 B1 | 10/2002 | Chishti et al. | |
| 6,554,611 B2 | 4/2003 | Chishti et al. | |
| 6,602,070 B2 | 8/2003 | Miller et al. | |
| 6,665,570 B2 | 12/2003 | Pavloskaia et al. | |
| 6,685,470 B2 | 2/2004 | Chishti et al. | |
| 6,688,886 B2 | 2/2004 | Hughes et al. | |
| 6,705,863 B2 | 3/2004 | Phan et al. | |
| 6,726,478 B1 | 4/2004 | Isiderio et al. | |
| 6,739,870 B2 | 5/2004 | Lai et al. | |
| 6,767,208 B2 | 7/2004 | Kaza | |
| 6,979,196 B2 | 12/2005 | Nikolskiy et al. | |
| 7,040,896 B2 | 5/2006 | Pavlovskaia et al. | |
| 7,059,850 B1 | 6/2006 | Phan et al. | |
| 7,063,532 B1 | 6/2006 | Jones et al. | |
| 7,123,767 B2 | 10/2006 | Jones et al. | |
| 7,125,248 B2 | 10/2006 | Phan et al. | |
| 7,134,874 B2 | 11/2006 | Chishti et al. | |
| 7,220,122 B2 | 5/2007 | Chishti | |
| 7,241,142 B2 | 7/2007 | Abolfathi et al. | |
| 7,293,988 B2 | 11/2007 | Wen | |
| 7,320,592 B2 | 1/2008 | Chishti et al. | |
| 7,373,286 B2 | 5/2008 | Nikolskiy et al. | |
| 7,377,778 B2 | 5/2008 | Chishti et al. | |
| 7,428,481 B2 | 9/2008 | Nikolskiy et al. | |
| 7,442,040 B2 | 10/2008 | Kuo | |
| 7,637,740 B2 | 12/2009 | Knopp | |
| 7,689,398 B2 | 3/2010 | Cheng et al. | |
| 7,771,195 B2 | 8/2010 | Knopp et al. | |
| 7,826,646 B2 | 11/2010 | Pavlovskaia et al. | |
| 7,841,858 B2 | 11/2010 | Knopp et al. | |
| 7,844,429 B2 | 11/2010 | Matov et al. | |
| 7,865,259 B2 | 1/2011 | Kuo et al. | |
| 7,904,307 B2 | 3/2011 | Abolfathi et al. | |
| 7,905,725 B2 | 3/2011 | Chishti et al. | |
| 7,942,672 B2 | 5/2011 | Kuo | |
| 7,993,134 B2 | 8/2011 | Wen | |
| 8,038,444 B2 | 10/2011 | Kitching et al. | |
| 8,044,954 B2 | 10/2011 | Kitching et al. | |
| 8,108,189 B2 | 1/2012 | Chelnokov et al. | |
| 8,131,393 B2 | 3/2012 | Matov et al. | |
| 8,135,569 B2 | 3/2012 | Matov et al. | |
| 8,244,390 B2 | 8/2012 | Kuo et al. | |
| 8,316,857 B2 | 11/2012 | Thornton | |
| 8,439,672 B2 | 5/2013 | Matov et al. | |
| 8,465,280 B2 | 6/2013 | Sachdeva et al. | |
| 8,478,435 B2 | 7/2013 | Kuo et al. | |
| 8,639,477 B2 | 1/2014 | Chelnokov et al. | |
| 8,641,414 B2 | 2/2014 | Borovinskih et al. | |
| 8,734,150 B2 | 5/2014 | Wen | |
| 8,780,106 B2 | 7/2014 | Chishti et al. | |
| 8,807,999 B2 | 8/2014 | Kuo et al. | |
| 8,896,592 B2 | 11/2014 | Boltunov et al. | |
| 8,897,902 B2 | 11/2014 | See et al. | |
| 8,961,173 B2 | 2/2015 | Miller | |
| 9,060,829 B2 | 6/2015 | Sterental et al. | |
| 9,107,722 B2 | 8/2015 | Matov et al. | |
| 9,161,823 B2 | 10/2015 | Morton et al. | |
| 9,211,166 B2 | 12/2015 | Kuo et al. | |
| 9,326,831 B2 | 5/2016 | Cheang | |
| 9,345,557 B2 | 5/2016 | Anderson et al. | |
| 9,375,293 B2 | 6/2016 | Taub et al. | |
| 9,375,300 B2 | 6/2016 | Matov et al. | |
| 9,414,897 B2 | 8/2016 | Wu et al. | |
| 9,433,476 B2 | 9/2016 | Khardekar et al. | |
| 9,529,970 B2 | 12/2016 | Andreiko | |
| 9,592,103 B2 | 3/2017 | Taub et al. | |
| 9,610,140 B2 | 4/2017 | Anderson et al. | |
| 9,622,834 B2 | 4/2017 | Chapoulaud et al. | |
| 9,792,413 B2 | 10/2017 | Badawi | |
| 9,844,424 B2 | 12/2017 | Wu et al. | |
| 10,011,050 B2 | 7/2018 | Kitching et al. | |
| 10,076,389 B2 | 9/2018 | Wu et al. | |
| 10,251,729 B1 * | 4/2019 | Raslambekov | A61C 7/36 |
| 10,307,222 B2 | 6/2019 | Morton et al. | |
| 10,332,164 B2 | 6/2019 | Abolfathi et al. | |
| 10,383,704 B2 | 8/2019 | Kitching | |
| 10,405,947 B1 | 9/2019 | Kaza et al. | |
| 10,405,951 B1 | 9/2019 | Kopelman et al. | |
| 10,413,385 B2 | 9/2019 | Sherwood et al. | |
| 10,433,934 B2 | 10/2019 | Kopelman | |
| 10,463,452 B2 | 11/2019 | Matov et al. | |
| 10,470,846 B2 | 11/2019 | Kopelman et al. | |
| 10,524,880 B2 | 1/2020 | Wen | |
| 10,553,309 B2 | 2/2020 | Trosien et al. | |
| 10,561,476 B2 | 2/2020 | Matov et al. | |
| 10,595,965 B2 | 3/2020 | Khardekar et al. | |
| 10,617,489 B2 | 4/2020 | Grove et al. | |
| 10,650,517 B2 | 5/2020 | Parpara et al. | |
| 10,653,503 B2 | 5/2020 | Boltunov et al. | |
| 10,783,629 B2 | 9/2020 | Parpara et al. | |
| 10,792,127 B2 | 10/2020 | Kopelman et al. | |
| 10,813,721 B2 | 10/2020 | Sterental et al. | |
| 2005/0244791 A1 | 11/2005 | Davis et al. | |
| 2009/0054897 A1 | 2/2009 | Gordon et al. | |
| 2010/0139666 A1 | 6/2010 | Bonnaure | |
| 2010/0154802 A1 | 6/2010 | Fuselier | |
| 2012/0145166 A1 * | 6/2012 | Fallon | A61F 5/566 128/848 |
| 2013/0081638 A1 * | 4/2013 | Petelle | A61F 5/566 128/848 |
| 2013/0095446 A1 | 4/2013 | Andreiko et al. | |
| 2013/0115567 A1 | 5/2013 | Jasper et al. | |
| 2013/0244195 A1 * | 9/2013 | Farrell | A61C 7/08 433/6 |
| 2013/0295514 A1 | 11/2013 | Koeklue et al. | |
| 2014/0120489 A1 | 5/2014 | Klein et al. | |
| 2014/0186788 A1 | 7/2014 | Sheibani et al. | |
| 2014/0288894 A1 | 9/2014 | Chishti et al. | |
| 2015/0059770 A1 | 3/2015 | Shah et al. | |
| 2015/0238284 A1 | 8/2015 | Wu et al. | |
| 2016/0302885 A1 | 10/2016 | Matov et al. | |
| 2017/0035536 A1 | 2/2017 | Alvarez Garcia et al. | |
| 2017/0056236 A1 | 3/2017 | Yousefian | |
| 2017/0079748 A1 | 3/2017 | Andreiko | |
| 2017/0100210 A1 | 4/2017 | Wen | |
| 2017/0135850 A1 | 5/2017 | Veis | |
| 2017/0290643 A1 | 10/2017 | Giardino | |
| 2018/0039755 A1 | 2/2018 | Matov et al. | |
| 2018/0078344 A1 | 3/2018 | Falkel | |
| 2018/0165818 A1 | 6/2018 | Tsai et al. | |
| 2018/0304497 A1 | 10/2018 | Kitching et al. | |
| 2019/0000592 A1 | 1/2019 | Cam et al. | |
| 2019/0046295 A1 | 2/2019 | Morton et al. | |
| 2019/0282333 A1 | 9/2019 | Matov et al. | |
| 2019/0314117 A1 | 10/2019 | Morton et al. | |
| 2019/0357997 A1 | 11/2019 | Shi et al. | |
| 2020/0000551 A1 | 1/2020 | Li et al. | |
| 2020/0000552 A1 | 1/2020 | Mednikov et al. | |
| 2020/0146776 A1 | 5/2020 | Matov et al. | |

(56) References Cited

U.S. PATENT DOCUMENTS

| | | |
|---|---|---|
| 2020/0229900 A1 | 7/2020 | Cunliffe et al. |
| 2020/0297459 A1 | 9/2020 | Grove et al. |
| 2020/0306012 A1 | 10/2020 | Roschin et al. |

FOREIGN PATENT DOCUMENTS

| | | |
|---|---|---|
| WO | 00019928 A1 | 4/2000 |
| WO | 00019930 A1 | 4/2000 |
| WO | 00019931 A1 | 4/2000 |
| WO | 00069356 A1 | 11/2000 |
| WO | 00069357 A1 | 11/2000 |
| WO | 01074268 A1 | 11/2001 |
| WO | 2017106896 A1 | 6/2017 |
| WO | 2018085718 A2 | 5/2018 |
| WO | 2019089989 A2 | 5/2019 |

OTHER PUBLICATIONS

Final European Search Report dated May 22, 2019 issued in respect of the counterpart European Patent Application No. 18192132.1.

\* cited by examiner

INTRA-ORAL DEVICE

CROSS-REFERENCE

The present application is a continuation application of U.S. patent application Ser. No. 16/119,068, filed Aug. 31, 2018, the entirety of which is incorporated herein by reference.

FIELD

The present technology relates to intra-oral devices, such as, but not limited to, orthodontic or pre-orthodontic appliances.

BACKGROUND

Intra-oral devices find many uses, such as in the areas of orthodontics for correcting malposed teeth and jaw; pre-orthodontic use for lip, tongue and facial muscle training and teeth and jaw alignment; medical therapy for preventing or treating snoring, obstructive sleep apnea or temporomandibular joint disorders; oral motor therapy such as for speech therapy; and protection of teeth, gums or jaws for example using mouthguards; smoking cessation; and weight control.

In the case of intra-oral devices for orthodontic and pre-orthodontic use, one such device type is known as a "trainer" and typically used in children. Trainers generally comprise an upper jaw applicator for receiving the teeth of the upper jaw in an upper channel defined by upper applicator walls, and a lower jaw applicator for receiving the teeth of the lower jaw in a lower channel defined by lower applicator walls. Some trainer types allow relative hinge-like movement between the upper and lower jaw applicators thereby allowing talking and chewing. Other trainer types have a fixed configuration between the upper and lower jaw applicators and are typically worn over the teeth during sleep. Trainers can have various other structural features, such as a lip guard for training overactive lip muscles, tongue tags for tongue placement training, and other structures for facial muscle training.

One design of trainer is illustrated in U.S. D 767,146 in which the upper and lower jaw applicators are provided as a single piece. As the size, shape and configuration of the upper and lower teeth vary significantly from patient to patient, such trainers are tailor-made for each patient by obtaining an impression of the teeth and making the trainer based on the teeth impression. The process of obtaining the impression is time consuming and uncomfortable for the patient. Particularly for children, this time, discomfort and resultant difficulty in obtaining an impression to make the trainer can be a deterrent for otherwise a useful treatment method.

For patients requiring correction of jaw defects, whether longitudinal or transverse, the treatment requires a number of adjustment steps over time, with each treatment step requiring a different size, shape or configuration of trainer. For each treatment step, a different trainer must be made for the patient, increasing their overall discomfort and in fact reducing the chances of finishing the treatment. Another confounding factor is that the rate of treatment is often prolonged, especially in the case of children, as they will only reliably wear the trainer at night.

It is an object of the present technology to ameliorate at least some of the inconveniences present in the prior art.

SUMMARY

Embodiments of the present technology have been developed based on developers' appreciation of certain shortcomings associated with the existing intra-oral devices. Some of these shortcomings include the necessity of having to tailor make intra-oral devices for each user in order to attain a satisfactory fit, or having to make additional intra-oral devices when a longitudinal and/or transverse adjustment is required during a treatment for example. Other shortcomings include the inability to adjust, longitudinal and/or transversely, the configuration of the intra-oral device during use by a user.

For example, one such intra-oral device of the prior art is for breathing assistance during sleep and is described in US 2012/0145166 (SnoreRX™). The device of US 2012/0145166 has an upper and lower jaw applicator and an adjustment therebetween for adjusting the distance between the upper and lower jaw applicators on a longitudinal plane. The mechanism is a ratchet-based mechanism which is released by exerting pressure on the lower jaw applicator and locked by releasing the applied pressure. In another intra-oral device for breathing assistance, the adjustment mechanism is a pin and hole system for adjusting the upper and lower jaw applicators relative to each other on a longitudinal plane (Twicare™). However, these prior art systems are limited to longitudinal adjustment.

Certain aspects and embodiments of the present technology, are directed to an intra-oral device which can be adjusted in one or more of a transverse direction, a longitudinal direction, and both a transverse and longitudinal direction. Certain embodiments of the presently developed intra-oral device is arranged to be received in a mouth of a user and to engage with at least some of the upper and lower teeth of the upper and lower jaws, respectively. The term "longitudinal direction" refers to an anterior-posterior anatomical direction, in use, and the term "transverse direction" refers to a lateral anatomical direction (transverse to a sagittal plane), in use. Therefore, in use, certain aspects and embodiments of the present technology can provide anterior-posterior and/or lateral adjustment of the user's teeth and/or jaws. In certain aspects and embodiments of the present technology, the intra-oral device is a one size fits all device and which can be adjusted transversely and/or longitudinally to engage with different sizes, shapes and configurations of teeth and jaws.

From one aspect, there is provided an intra-oral device comprising: an upper jaw applicator and a lower jaw applicator, the upper jaw applicator comprising an upper left component and an upper right component, and the lower jaw applicator comprising a lower left component and a lower right component; a transverse adjustment mechanism for simultaneously adjusting a distance between: the upper left component and the upper right component, and the lower left component and the lower right component, wherein the transverse adjustment mechanism comprises: a threaded rod having two end portions, one end portion of the threaded rod being engageable with the upper left component and the lower left component, and the other end portion of the threaded rod engageable with the upper right component and the lower right component.

In certain embodiments, the intra-oral device comprises an adjustment member for effecting rotation of the threaded rod about a longitudinal axis of the threaded rod, wherein the adjustment member comprises at least one opening positioned along the threaded rod, the at least one opening being engageable with a tool for effecting the rotation of the threaded rod.

In certain embodiments, the intra-oral device further comprises lower threads on an upper face of the lower jaw applicator, and upper threads on a lower face of the upper jaw applicator, the upper threads extending across at least a portion of one or both of the upper left component and the upper right component, and the lower threads extending across at least a portion of one or both of the lower left component and lower right component, wherein the threaded rod is engageable with the lower threads and the upper threads.

In certain embodiments, the upper threads and the lower threads are each formed on a respective plate which is attached to the respective lower and upper faces of the upper jaw applicator and the lower jaw applicator, respectively.

In certain embodiments, one or both of the upper threads and the lower threads are formed directly in the respective lower and upper faces of the upper jaw applicator and the lower jaw applicator.

In certain embodiments, the intra-oral device further comprises a longitudinal adjustment mechanism for adjusting a relative longitudinal position of the upper jaw applicator to the lower jaw applicator.

In certain embodiments, the longitudinal adjustment mechanism comprises a linear ratchet mechanism on a longitudinal plane of the intra-oral device, the linear ratchet mechanism comprising: a rack of teeth, the teeth being spaced along a longitudinal edge of the rack of teeth, and a dowel having a dowel member arranged to inter-engage with the teeth of the rack of teeth.

In certain embodiments, the rack of teeth is associated with an upper face of the lower jaw applicator, and the dowel is associated with the upper jaw applicator.

In certain embodiments, the longitudinal adjustment mechanism further comprises a locking mechanism for maintaining the dowel in engagement with the teeth, the locking mechanism comprising a biasing member for providing a resilient bias to the dowel towards a base of the teeth along the longitudinal edge of the rack of teeth.

In certain embodiments, the intra-oral device comprises a guide, associated with the upper jaw applicator and the lower jaw applicator, for guiding a longitudinal movement of the upper jaw applicator relative to the lower jaw applicator, the guide comprising at least one guide rail which can be slidingly received in an associated at least one guide slot.

In certain embodiments, the at least one guide rail is provided protruding from, and extending along at least a portion of, an upper face of the lower jaw applicator, and the associated the at least one guide slot is defined in a lower face of the upper jaw applicator.

In certain embodiments, the intra-oral device includes a silicon-based covering.

In certain embodiments, each of the upper jaw applicator and the lower jaw applicator comprise a base and walls defining a channel for receiving at least some teeth of a user in use.

From another aspect, there is provided an intra-oral device comprising an upper jaw applicator and a lower jaw applicator, the upper jaw applicator comprising a base and walls defining a channel for receiving at least some upper teeth of a user in use, and configured as an upper left quadrant and an upper right quadrant; the lower jaw applicator comprising a base and walls defining a channel for receiving at least some lower teeth of the user in use, and configured as a lower left quadrant and a lower right quadrant, a transverse adjustment mechanism arranged to engage with each of the upper left quadrant, the upper right quadrant, the lower left quadrant and the lower right quadrant in order to simultaneously adjust a transverse distance between the upper right quadrant and the upper left quadrant, and between the lower right quadrant and the lower left quadrant.

In certain embodiments, the transverse adjustment mechanism comprises a threaded rod having two end portions, one end portion of the threaded rod being engageable with the upper left quadrant and the lower left quadrant, and the other end portion of the threaded rod engageable with the upper right quadrant and the lower right quadrant.

In certain embodiments, the intra-oral device further comprises an adjustment member for effecting rotation of the threaded rod about a longitudinal axis of the threaded rod, wherein the adjustment member comprises at least one opening positioned along the threaded rod, the at least one opening being engageable with a tool for effecting the rotation of the threaded rod.

In certain embodiments, the intra-oral device further comprises lower threads on an upper face of the lower jaw applicator and upper threads on a lower face of the upper jaw applicator, the upper threads extending across at least a portion of one or both of the upper left and upper right quadrants, and the lower threads extending across at least a portion of one or both of the lower left and lower right quadrants, wherein the threaded rod is engageable with the lower threads and the upper threads in use.

In certain embodiments, the intra-oral device further comprises a longitudinal adjustment mechanism for adjusting a relative longitudinal position of the upper jaw applicator to the lower jaw applicator, wherein the longitudinal adjustment mechanism comprises a linear ratchet mechanism on a longitudinal plane of the intra-oral device, the linear ratchet mechanism comprising: a rack of teeth, the teeth of the rack of teeth being spaced along a longitudinal edge of the rack of teeth, and a dowel having a dowel member arranged to inter-engage with the teeth of the rack of teeth.

In certain embodiments, the longitudinal adjustment mechanism further comprises a locking mechanism for maintaining the dowel in engagement with the teeth of the rack of teeth, the locking mechanism comprising a biasing member for providing a resilient bias to the dowel towards a base of the teeth of the rack of teeth along the longitudinal edge of the rack of teeth.

From one aspect, there is provided an intra-oral device comprising: an upper jaw applicator and a lower jaw applicator, a longitudinal adjustment mechanism for adjusting a relative longitudinal position of the upper jaw applicator to the lower jaw applicator, and a transverse adjustment mechanism for adjusting a distance between lateral sides of the upper and lower jaw applicators.

In certain embodiments, the transverse adjustment mechanism is arranged to adjust the distance between the lateral sides of the upper and lower jaw applicators simultaneously.

In certain embodiments, the upper jaw applicator comprises an upper left component and an upper right component, and the lower jaw applicator comprises a lower left component and a lower right component, the transverse adjustment mechanism being arranged to adjust the distance between one or both of:
(a) the upper left component and the upper right component, and
(b) the lower left component and the lower right component.

In certain embodiments, the transverse adjustment mechanism is arranged to simultaneously adjust the distance between:
(a) the upper left component and the upper right component, and
(b) the lower left component and the lower right component.

In certain embodiments, the transverse adjustment mechanism comprises:

a threaded rod having two end portions, one end portion of the threaded rod being engageable with a thread on the upper left component and a thread on the lower left component of the intra-oral device, and the other end portion of the threaded rod engageable with a thread on the upper right component and a thread on the lower right component of the intra-oral device; and an adjustment member for effecting rotation of the threaded rod about a longitudinal axis of the threaded rod.

In certain embodiments, the transverse adjustment mechanism comprises:

a threaded rod having two end portions, one end portion of the threaded rod being engageable with a thread on a left component of the intra-oral device and the other end portion of the threaded rod being engageable with a thread on a right component of the intra-oral device; and an adjustment member for effecting rotation of the threaded rod about a longitudinal axis of the threaded rod.

In certain embodiments, the left component of the intra-oral device comprises one or both of the upper left component of the upper jaw appliance and the lower left component of the lower jaw appliance.

In certain embodiments, the right component of the intra-oral device comprises one or both of the upper right component of the upper jaw appliance and the lower right component of the lower jaw appliance.

In certain embodiments, the adjustment member comprises at least one opening positioned on the threaded rod, the at least one opening being engageable with a tool for effecting the rotation of the threaded rod. In certain embodiments, the at least one opening is positioned about midway along a length of the threaded rod. The opening may be defined in the threaded rod or in a sleeve attachable to the threaded rod.

In certain embodiments, the transverse adjustment mechanism comprises:

a threaded rod having two end portions, one end portion of the threaded rod being engageable with a thread on a left component of the intra-oral device, and the other end portion of the threaded rod engageable with a thread on a right component of the intra-oral device; and an adjustment member for effecting rotation of the threaded rod about a longitudinal axis of the threaded rod.

In certain embodiments, the longitudinal adjustment mechanism comprises a linear ratchet mechanism on a longitudinal plane of the intra-oral device, the linear ratchet mechanism comprising:

a rack of teeth spaced along a longitudinal edge of the rack, and a dowel arranged to inter-engage with the teeth.

In certain embodiments, the linear ratchet mechanism is associated with the upper face of the lower jaw applicator, and the dowel is associated with the upper jaw applicator.

In certain embodiments, the longitudinal adjustment mechanism further comprises a locking mechanism for maintaining the dowel in engagement with the teeth, the locking mechanism comprising a biasing member for providing a resilient bias to the dowel towards a base of the teeth along a longitudinal edge of the rack.

In certain embodiments, the intra-oral device further comprises a guide, associated with the upper jaw applicator and the lower jaw applicator, for guiding a longitudinal movement of the upper jaw applicator relative to the lower jaw applicator, the guide comprising a at least one guide rail which can be slidingly received in an associated at least one guide slot.

In certain embodiments, the at least one guide rail is provided protruding from, and extending along at least a portion of, an upper face of the lower jaw applicator, and the associated the at least one guide slot is defined in a lower face of the upper jaw applicator.

In certain embodiments, the guide rail has a base portion and a top portion, the top portion being wider than the base portion.

In certain embodiments, the intra-oral device comprises a base material and a coating material. The base material may be a metal frame. The coating may be made of a biocompatible material. In certain embodiments, the intra-oral device includes a silicon-based coating.

In certain embodiments, each of the upper jaw applicator and the lower jaw applicator comprises a base and walls defining a channel for receiving at least some teeth of a user in use. In certain embodiments, the channel is arcuate.

From another aspect, there is provided an intra-oral device comprising: an upper jaw applicator and a lower jaw applicator, a transverse adjustment mechanism for adjusting a distance between lateral sides of the upper and lower jaw applicators, wherein the transverse adjustment mechanism comprises: a threaded rod having two end portions, one end portion of the threaded rod being engageable with a thread on a left component of the intra-oral device, and the other end portion of the threaded rod engageable with a thread on a right component of the intra-oral device; and an adjustment member for effecting rotation of the threaded rod about a longitudinal axis of the threaded rod.

In certain embodiments, the left component comprises an upper left component of the upper jaw applicator and a lower left component of the lower jaw applicator, and the right component comprises an upper right component of the upper jaw applicator and a lower right component of the lower jaw applicator.

In certain embodiments, the adjustment member comprises at least one opening defined along the threaded rod, the at least one opening being engageable with a tool for effecting the rotation of the threaded rod. In certain embodiments, the at least one opening is defined about midway along a length of the threaded rod.

From another aspect, there is provided an intra-oral device comprising: an upper jaw applicator and a lower jaw applicator, a longitudinal adjustment mechanism for adjusting a relative longitudinal position of the upper jaw applicator to the lower jaw applicator, wherein the longitudinal adjustment mechanism comprises: a linear ratchet mechanism on a longitudinal plane of the intra-oral device, the linear ratchet mechanism comprising: a rack of teeth spaced along a longitudinal edge of the rack, and a dowel arranged to inter-engage with the teeth.

In certain embodiments, the longitudinal adjustment mechanism further comprises a locking mechanism for maintaining the dowel in engagement with the teeth, the locking mechanism comprising a biasing member for providing a resilient bias to the dowel towards a base of the teeth along a longitudinal edge of the rack.

In certain embodiments, the linear ratchet mechanism is associated with the upper face of the lower jaw applicator, and the dowel is associated with the upper jaw applicator.

In certain embodiments, the intra-oral device further comprises a guide, associated with the upper jaw applicator and the lower jaw applicator, for guiding a longitudinal movement of the upper jaw applicator relative to the lower jaw applicator, the guide comprising a at least one guide rail which can be slidingly received in an associated at least one guide slot.

In certain embodiments, the at least one guide rail is provided protruding from, and extending along at least a portion of, an upper face of the lower jaw applicator, and the associated the at least one guide slot is defined in a lower face of the upper jaw applicator.

In certain embodiments, the guide rail has a base portion and a top portion, the top portion being wider than the base portion.

In certain embodiments, the intra-oral device has a silicon-based coating.

In certain embodiments, wherein each of the upper jaw applicator and the lower jaw applicator comprises a base and walls defining a channel for receiving at least some teeth of a user in use.

In certain embodiments, the intra-oral device comprises the longitudinal adjustment mechanism without the transverse adjustment mechanism. In certain embodiments, the intra-oral device comprises the transverse adjustment mechanism without the longitudinal adjustment mechanism. In certain embodiments, the intra-oral device comprises both the transverse adjustment mechanism and the longitudinal adjustment mechanism.

In certain embodiments, the intra-oral device provides an ability to adjust a longitudinal distance between upper and lower jaw appliances using the horizontal adjustment mechanism. In certain embodiments, the longitudinal adjustment can be made in incremental distances and locked using the locking means. The configuration of the transverse adjustment mechanism, in certain embodiments, allows an appropriate locking of the adjusted position of the upper and lower jaw appliances such that a locked position cannot easily or accidentally unlocked, in use, in the mouth of a user. Advantageously, the longitudinal adjustment mechanism can be readily moved to the released position, when desired.

In certain embodiments, the intra-oral device provides an ability to adjust a distance between lateral sides of the device using the transverse adjustment mechanism. In certain embodiments, the lateral sides of the upper jaw applicator and the lower jaw applicator can both be adjusted using the transverse adjustment. The lateral adjustment of the upper jaw applicator and the lower jaw applicator can occur simultaneously. In certain embodiments, transverse adjustment of one of the upper and lower jaw applicators can effect transverse adjustment of the other of the upper and lower jaw applicators.

In certain embodiments, the intra-oral device is adjustable in both the transverse and longitudinal directions. This combination of directional control allows the provision of a large number of upper jaw/lower jaw configurations. In certain uses, the intra-oral device is an effective one-size fits all device suitable for a large number of users with different and unique jaw configurations. In orthodontic uses, for example, the intra-oral device can be initially configured so that it fits the malposed jaw/teeth configuration of the user. The upper and/or lower jaw applicators can then be gradually and incrementally moved to position the jaws/teeth in a desired position. In breathing assistance uses, for example, the intra-oral device may be adjusted initially to fit the user thereby avoiding discomfort associated with an ill-fitting intra-oral device. Further adjustments to the intra-oral device may or may not be required depending on the application.

In the context of the present specification, unless expressly provided otherwise, an intra-oral device may refer to, but is not limited to, any type of device positionable in the mouth of a patient, including but not limited to orthodontic and pre-orthodontic devices, protective devices such as mouthguards, breathing assistance devices such as for snoring, sleep apnea or TMJ, other medical therapy devices such as for oral motor therapy, and/or any combination thereof.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Implementations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

It should be noted that, unless otherwise explicitly specified herein, the drawings are not to scale.

DETAILED DESCRIPTION

The present technology is not limited in its use, and can be used for any purpose requiring adjustment of upper and lower jaws or teeth in one or more of the transverse direction, the longitudinal direction and the transverse and longitudinal directions, and/or for any purpose in which adjustment of an intra-oral device 10 is required to fit a certain anatomical configuration of a user.

Examples of certain uses of the present technology include, but are not limited to, any of an orthodontic trainer, a pre-orthodontic trainer, a breathing assistant, a mouthguard, a speech therapy device, a muscle training device, a smoking cessation device, a weight control device, or the like.

Figure 6:
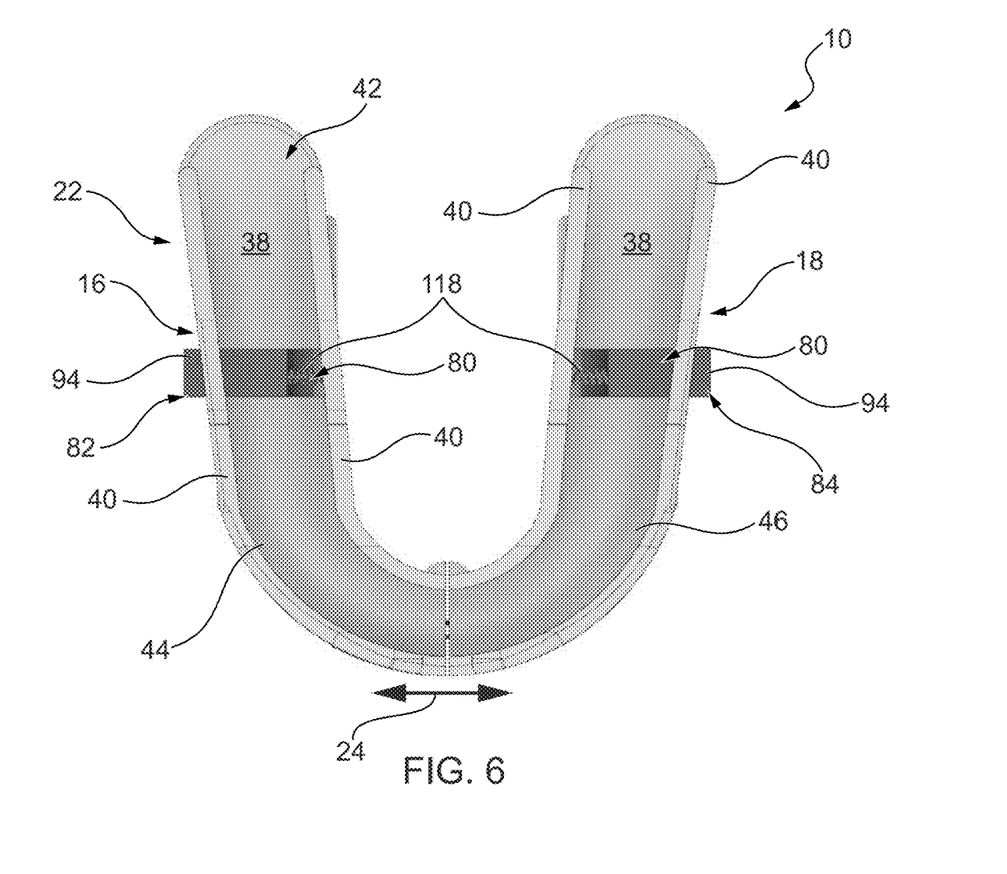
FIG. 6 is a bottom view of the intra-oral device of FIG. 1.
Figure 7:
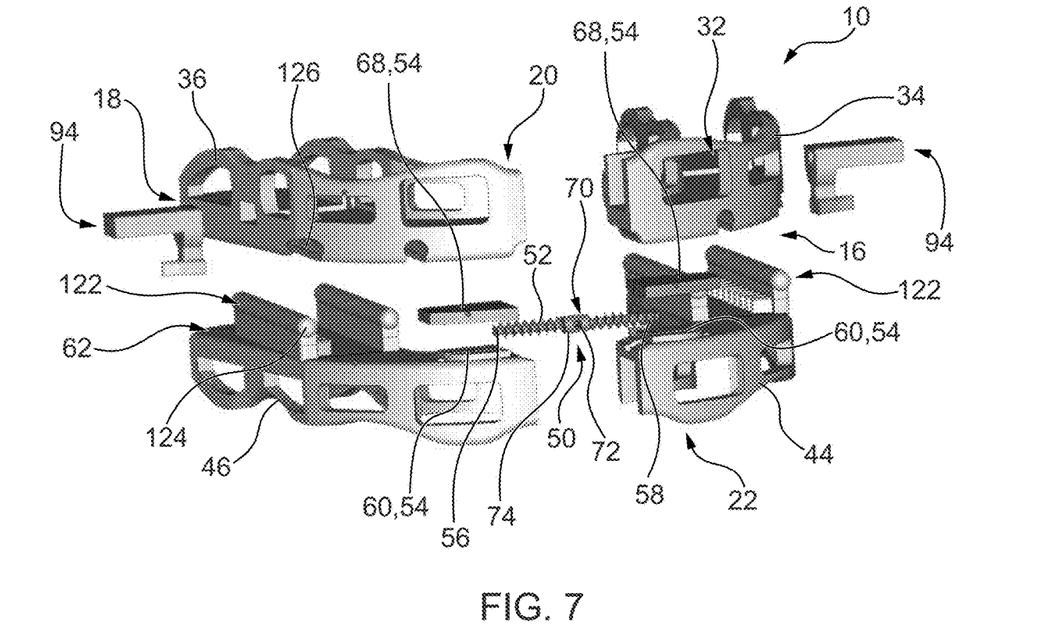
FIG. 7 is an exploded view of the intra-oral device of FIG. 1 when viewed from the front and top.
Figure 8:
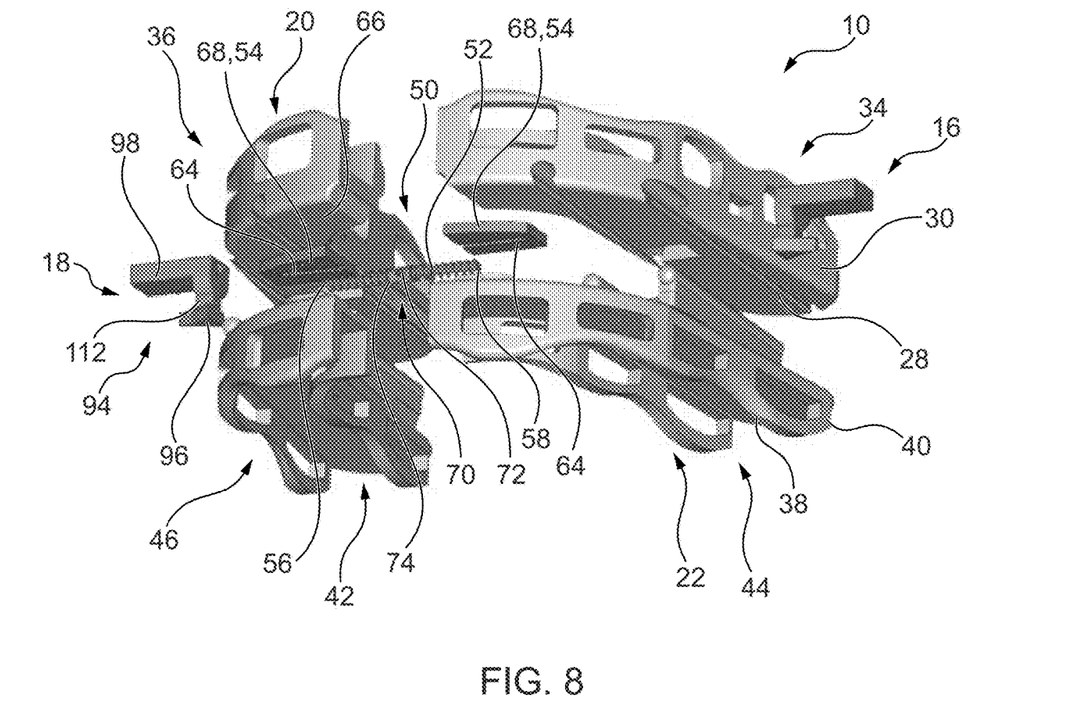
FIG. 8 is an exploded view of the intra-oral device of FIG. 1 when viewed from the front and bottom.
Figure 9:
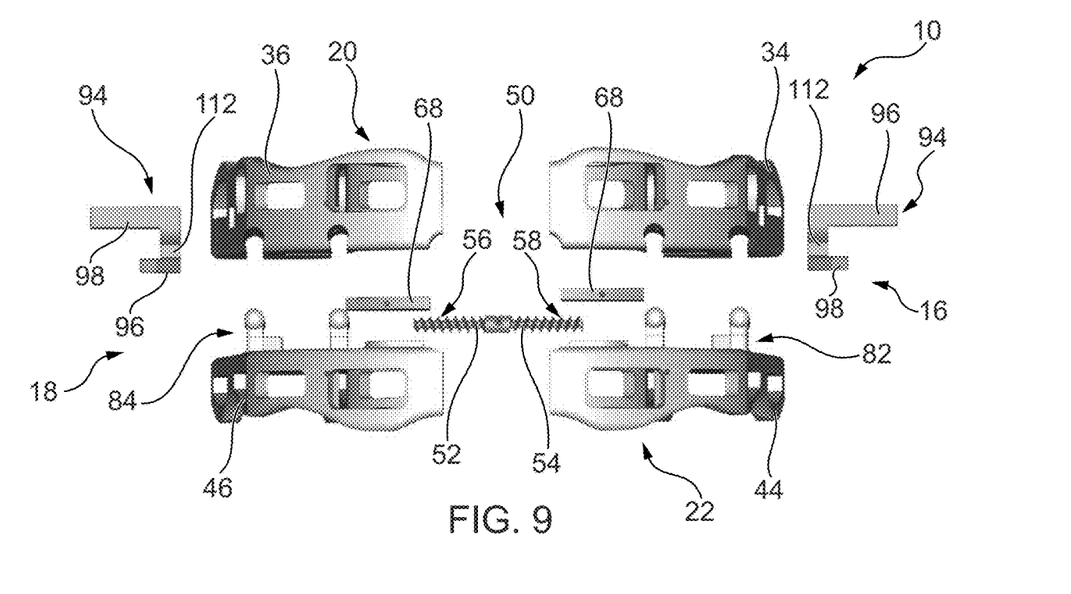
FIG. 9 is an exploded view of the intra-oral device of FIG. 1 when viewed from the front.

Referring initially to FIGS. 1 to 9, there is shown an embodiment of the intra-oral device 10 having a front end 12 (also referred to as anterior end, in use), a back end 14 (also referred to as posterior end, in use), and two lateral sides 16, 18 (a left side and a right side). The intra-oral device 10 comprises an upper jaw applicator 20 and a lower jaw applicator 22. The upper and lower jaw applicators 20, 22 can be adjusted relative to each other in one or both of a transverse 24 and a longitudinal direction 26 (FIGS. 6 and 7).

The upper jaw applicator 20 comprises an upper applicator base 28 and upper applicator walls 30 which together define an upper applicator channel 32. The upper jaw applicator 20 has an arcuate form (U-shaped) for generally following a typical upper jaw contour. The upper applicator channel 32 is arranged to receive at least some of the top teeth of a user, with the user's molars or other back teeth being positioned at or near the back end 14, and the user's front teeth being received at or near the front end 12. The upper applicator channel 32 is open ended at the back end 14.

The upper jaw applicator 20 is in two halves, and comprises an upper left component 34 and an upper right component 36 which can be moved, transversely away and towards each other, in a manner that will be described below. Such transverse 24 movement adjusts a distance between the lateral sides 16, 18 of the intra-oral device 10.

The lower jaw applicator 22 comprises a lower applicator base 38 and lower applicator walls 40 which together define a lower applicator channel 42. The lower jaw applicator 22 has an arcuate form (U-shaped) for generally following a typical lower jaw contour. The lower applicator channel 42 is arranged to receive at least some of the lower teeth of a user, with the user's molars or other back teeth being positioned at or near the back end 14, and the user's front teeth being received at or near the front end 12. The lower applicator channel 42 is open ended at the back end 14.

Figure 1:
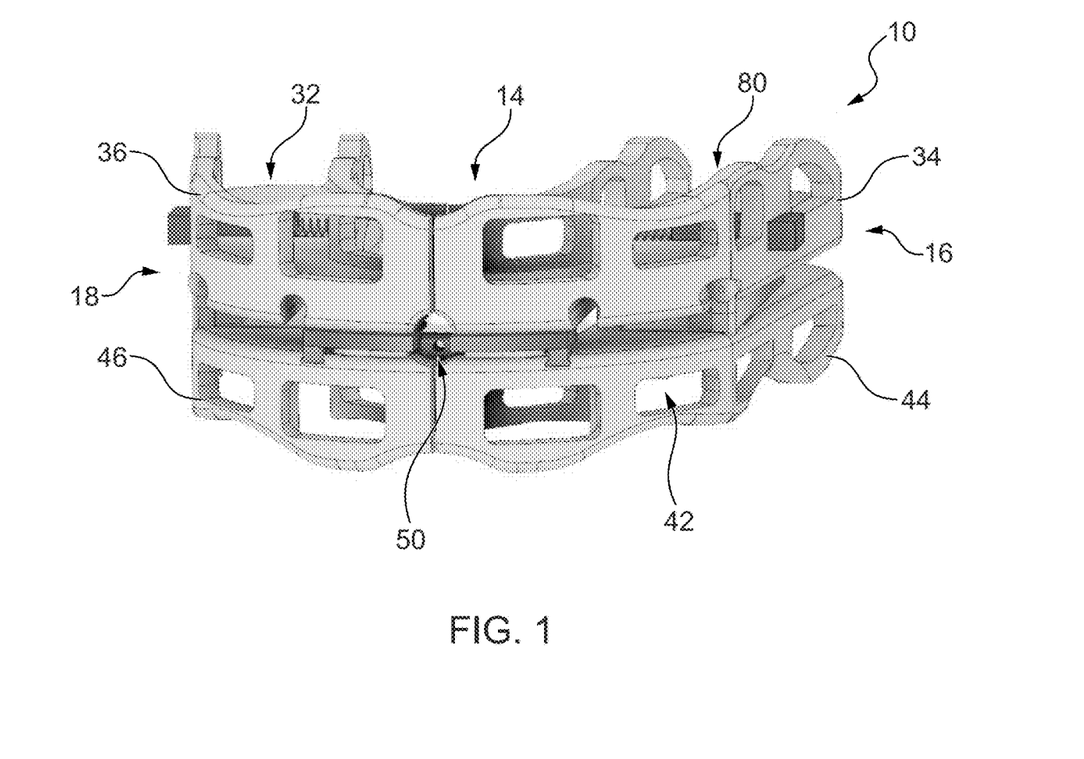
FIG. 1 is a perspective view from a front of an intra-oral device according to certain embodiments of the technology.
Figure 2:
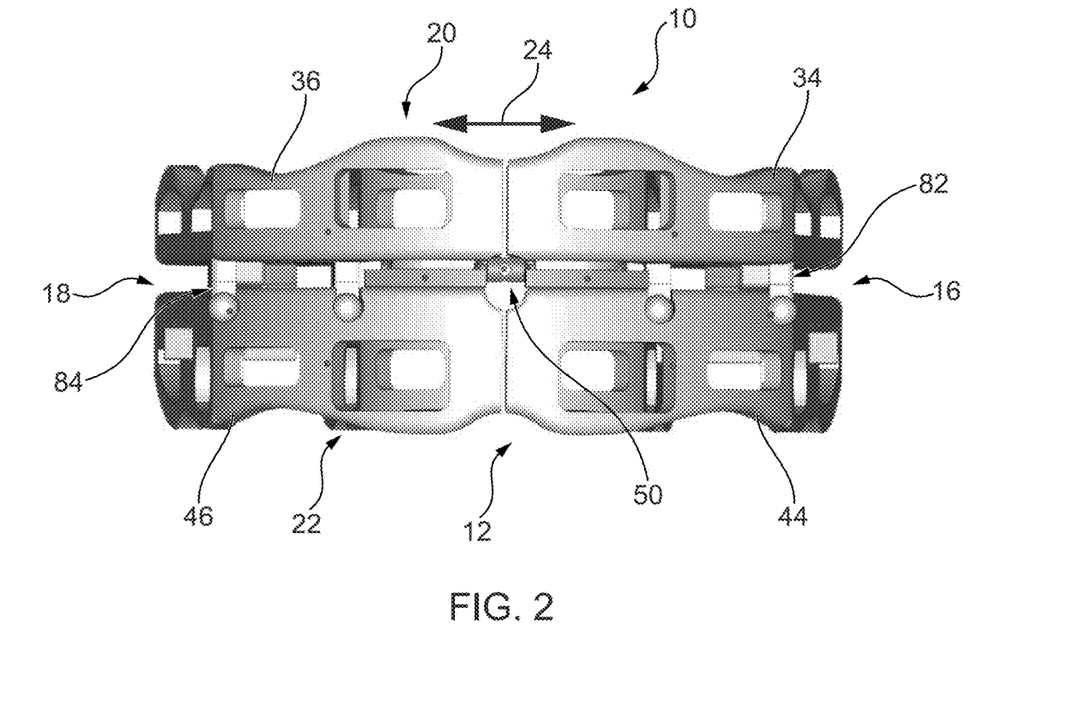
FIG. 2 is a front elevational view of the intra-oral device of FIG. 1.
Figure 3:
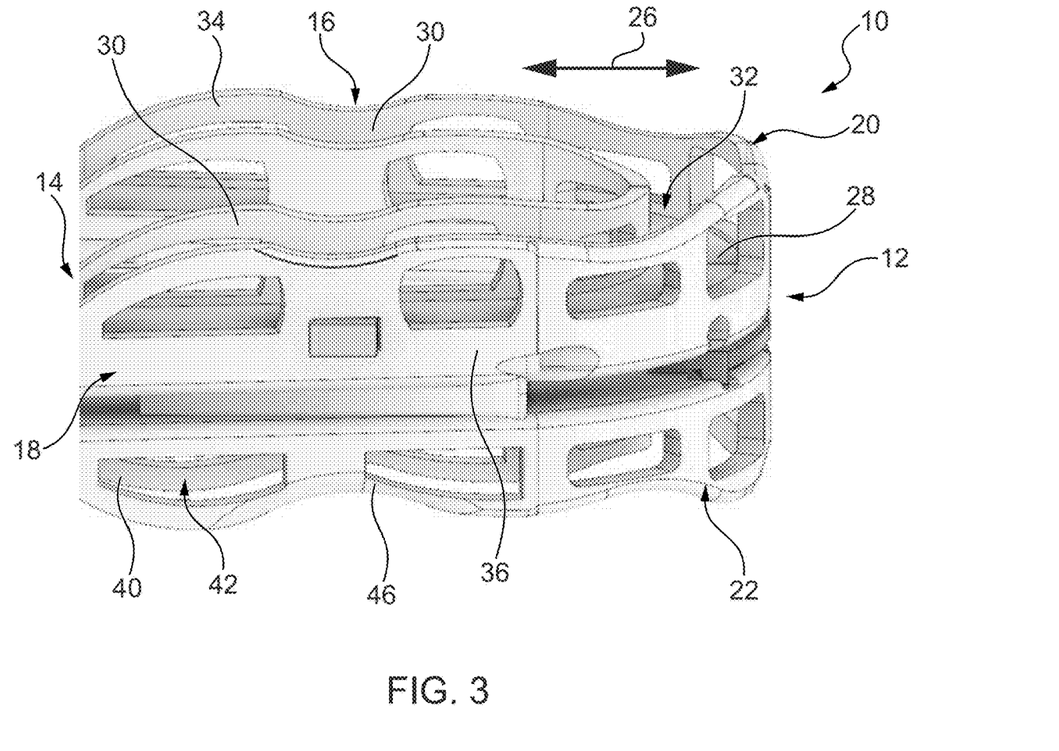
FIG. 3 is a right side view of the intra-oral device of FIG. 1.
Figure 4:
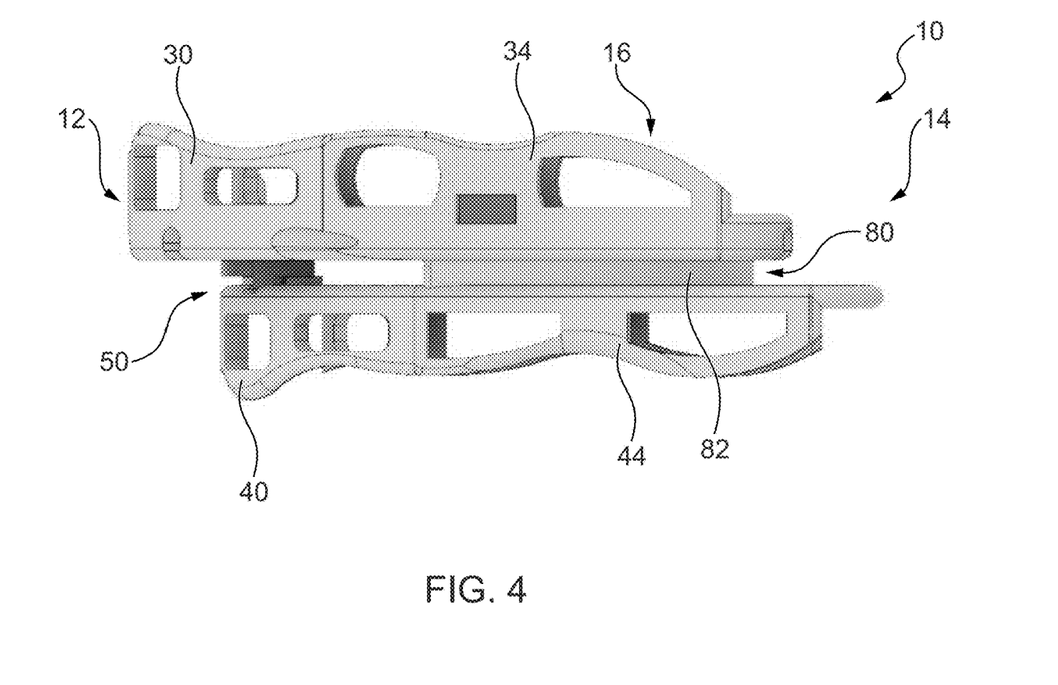
FIG. 4 is a left side view of the intra-oral device of FIG. 1, with an upper jaw applicator positioned forwardly of a lower jaw applicator.
Figure 5:
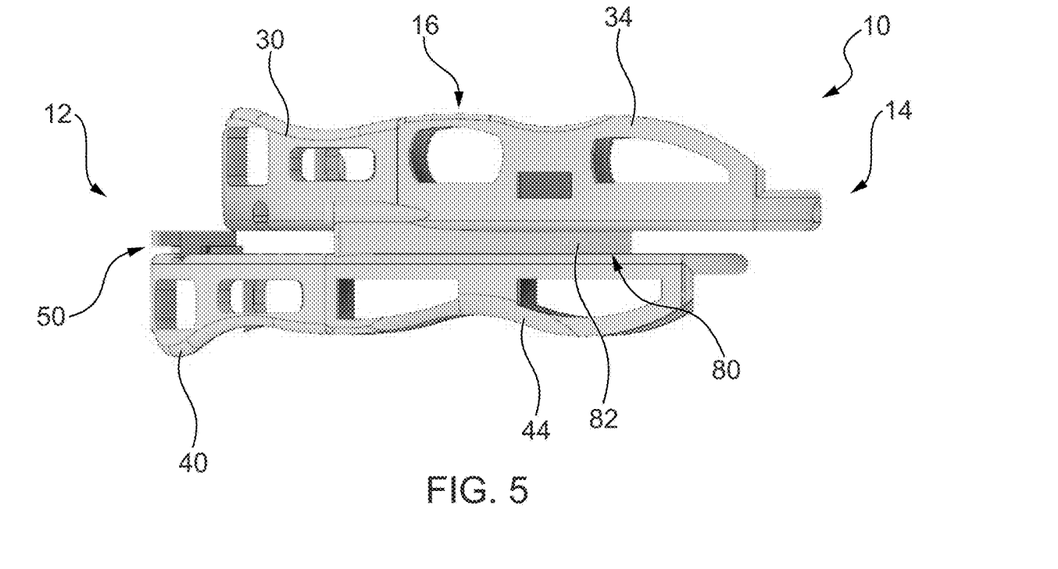
FIG. 5 is a left side view of the intra-oral device of FIG. 1, with an upper jaw applicator positioned rearwardly of a lower jaw applicator.

The lower jaw applicator 22 is in two halves, and comprises a lower left component 44 and a lower right component 46 which can be moved transversely 24, away and towards each other, in a manner that will be described below (FIGS. 2 and 6).

The intra-oral device 10 is provided with a transverse adjustment mechanism 50. The transverse adjustment mechanism 50 is arranged to adjust a distance between the lateral sides 16, 18 of the upper and lower jaw applicators 20, 22 as movement in a transverse direction 24. In certain embodiments, the transverse adjustment mechanism 50 is arranged to cause the transverse movement of the upper and lower jaw applicators 20, 22 at the same time. In certain embodiments, by "the same time" or simultaneously, it is meant that a single adjustment action to the transverse adjustment mechanism causes a transverse movement in both the upper and lower jaw applicators 20, 22. Specifically, the transverse adjustment mechanism 50 is arranged to cause transverse movement of the lower left component 44 relative to the lower right component 46 of the lower jaw applicator 22. The transverse adjustment mechanism 50 is also arranged to cause transverse movement of the upper left component 34 and the upper right component 36 of the upper jaw applicator 20.

In certain other embodiments, the transverse adjustment mechanism 50 is arranged to cause the transverse 24 movement of the upper and lower jaw applicators 20, 22 separately.

The upper left component 34, the upper right component 36, the lower left component 44, and the lower right component 46 can be considered as quadrants of the intra-oral device 10. As can be best seen in the exploded views of FIGS. 7 to 9, the transverse adjustment mechanism 50 is arranged to engage with each of the quadrants of the intra-oral device 10 such that actuation of the transverse adjustment mechanism 50 causes transverse movement of the upper quadrants and the lower quadrants, which can occur simultaneously.

The transverse adjustment mechanism 50 comprises a threaded rod 52 that engages with threads 54 on oppositely facing faces of the upper jaw applicator 20 and the lower jaw applicator 22. Specifically, the threaded rod 52 has two end portions 56, 58, one end portion 56 of the threaded rod 52 is engageable with the upper left component 34 and the lower left component 44 of the intra-oral device 10, and the other end 58 of the threaded rod 52 is engageable with the upper right component 36 and the lower right component 46 of the intra-oral device 10.

In certain embodiments, the threaded rod 52 is a dowel screw, a double-ended screw, a threaded stud, or the like. The threads 54 comprise lower threads 60 provided on an upper face 62 of the lower jaw applicator 22, and upper threads 64 provided on a lower face 66 of the upper jaw applicator 20. The upper threads 64 extend across at least a portion of one or both of the upper left and upper right components 34, 36. Similarly, the lower threads 60 extend across at least a portion of one or both of the lower left and lower right components 44, 46. The upper and lower threads 64, 60 are each formed on a respective plate 68 which is attached to the respective lower and upper faces 66, 62 of the upper jaw applicator 20 and the lower jaw applicator 22, respectively. In certain other embodiments, one or both of the upper and lower threads 64, 60 can be formed directly in the respective lower and upper faces 66, 62 of the upper jaw applicator 20 and the lower jaw applicator 22.

An adjustment member 70 is provided along a length of the threaded rod 52 for allowing rotation of the threaded rod 52 about its longitudinal axis. The adjustment member 70 comprises an opening 72 defined about midway along the length of the threaded rod, between the left and right quadrants, the opening 72 being engageable with a tool (not shown) to enable the rotation of the threaded rod 52. In the illustrated embodiment, the adjustment member 70 comprises a sleeve 74 in which the opening 72 is formed. The tool (now shown) can be any appropriate tool having a handle at one end and a protrusion at the other end for engagement with the opening of the adjustment member 70. The opening 72 and the protrusion may take any shape or form such as a circle, a hexagon, a triangle, a square or the like.

In use, rotation of the threaded rod 52 causes the left and right quadrants of the upper and lower jaw applicators 20, 22 to be brought closer or further apart due to engagement of the threaded rod 52 with the threads 54 of the left and right quadrants. This transverse movement between the left and right quadrants can occur at the same time with a single adjustment of the transverse adjustment mechanism 50. For the avoidance of doubt, the left quadrant of the intra-oral device 10 comprises the upper left component 34 of the upper jaw applicator 20 and the lower left component 44 of the lower jaw applicator 22. The right quadrant of the intra-oral device 10 comprises the upper right component 36 of the upper jaw applicator 20 and the lower right component 46 of the lower jaw applicator 22. Transverse movement of the left and right quadrants away from each other widens a distance between the lateral sides 16, 18 of the intra-oral device 10 which can induce a palate widening of the user, in use.

In certain embodiments, a transverse adjustment between the left and right quadrants of up to about 6 mm can be obtained.

Figure 10:
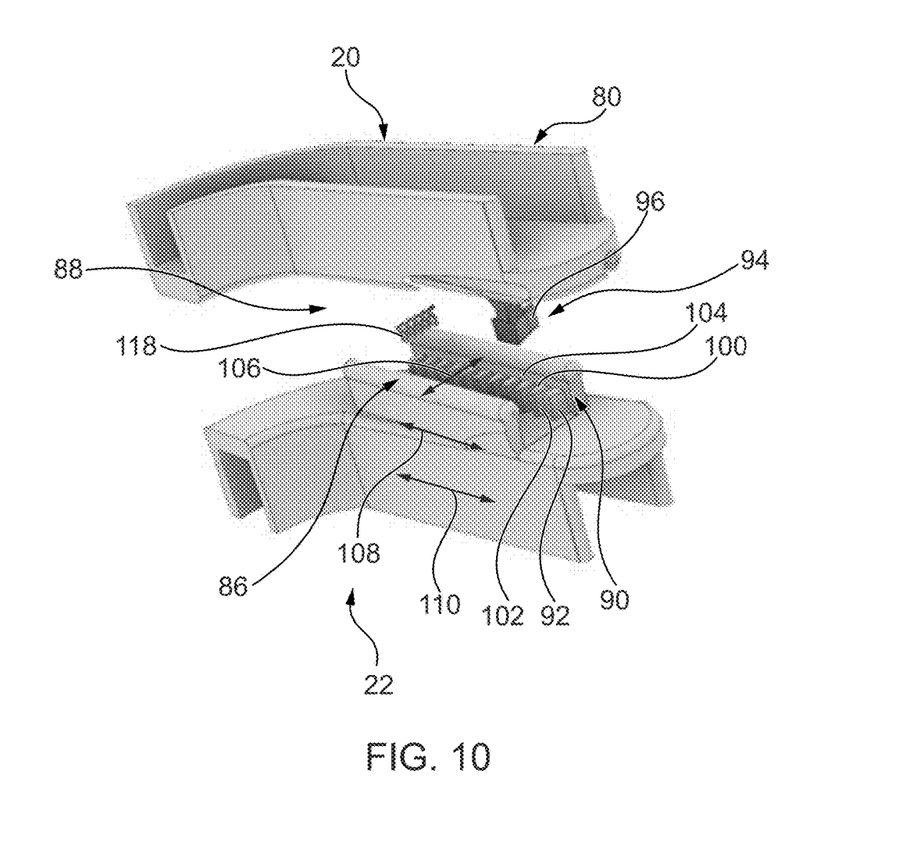
FIG. 10 is an enlarged portion of an exploded view from the bottom of the intra-oral device of FIG. 1, with portions removed for clarity, showing a longitudinal adjustment mechanism of the intra-oral device according to certain embodiments of the present technology.
Figure 11:
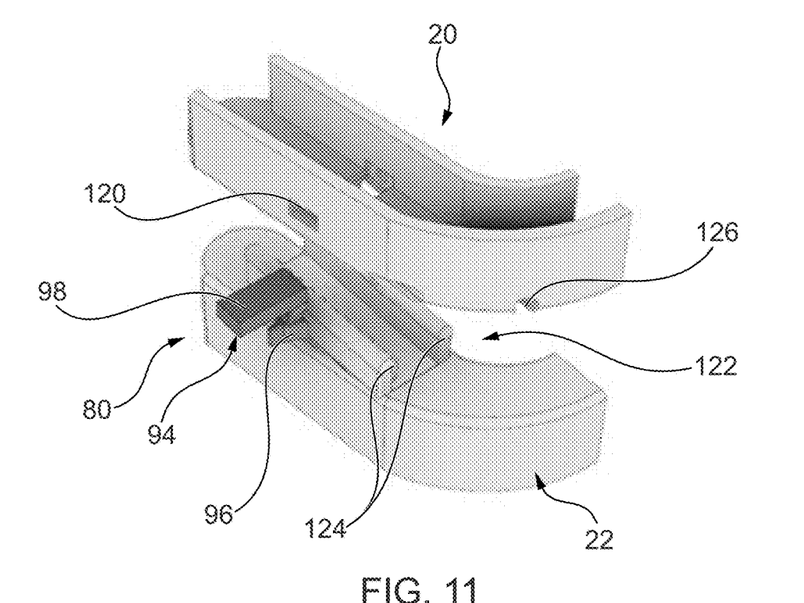
FIG. 11 is an enlarged portion of an exploded view from the top of the intra-oral device of FIG. 1, with portions removed for clarity, showing a longitudinal adjustment mechanism of the intra-oral device according to certain embodiments of the present technology.
Figure 12:
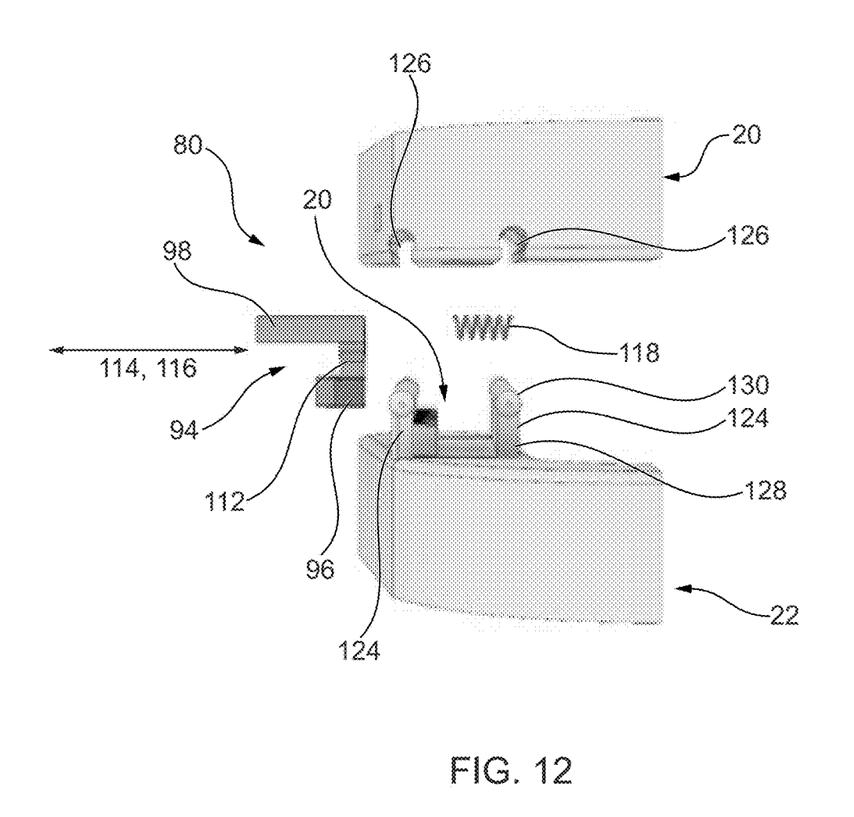
FIG. 12 is an enlarged portion of an exploded view from the front of the intra-oral device of FIG. 1, with portions removed for clarity, showing a longitudinal adjustment mechanism of the intra-oral device according to certain embodiments of the present technology.

Turning now to FIGS. 10 to 12, the intra-oral device 10 is also provided with a longitudinal adjustment mechanism 80. The longitudinal adjustment mechanism 80 is arranged to effect longitudinal movement in a longitudinal direction 26 of the upper and lower jaw applicators 20, 22 relative to one another. The longitudinal adjustment mechanism 80 comprises two longitudinal adjustment mechanism units which operate in the same fashion: a left longitudinal adjustment mechanism 82 acting between the left quadrants of the intra-oral device 10, and a right longitudinal adjustment mechanism 84 acting between the right quadrants of the intra-oral device 10.

The left and right longitudinal adjustment mechanisms 82, 84 operate in the same way and will be described below with reference to the longitudinal adjustment mechanism 80. The longitudinal adjustment mechanism 80 comprises a ratchet mechanism 86 and a locking mechanism 88.

The ratchet mechanism 86 is a linear ratchet mechanism, along a longitudinal plane, which comprises inter-engaging elements acting between the upper face 62 of the lower jaw applicator 22 and the lower face 66 of the upper jaw applicator 20. The ratchet mechanism 86 comprises a rack 90 of linearly spaced apart teeth 92 and a dowel 94 arranged to inter-engage with the teeth 92. Specifically, the dowel 94 comprises a dowel member 96 for engagement with the teeth 92 or with spaces defined between the teeth, and a dowel adjustment arm 98 for moving the longitudinal adjustment mechanism 80 between a locked position and a release position. The inter-engaging elements comprise the dowel member 96 and the teeth 92 of the rack 90.

In the illustrated embodiments, the rack of teeth 90 extends along at least a portion of the upper face 62 of the lower jaw applicator 22, and protrudes upwardly therefrom. The teeth 92 are linearly spaced apart but could also take any other spacing configuration dependant on the desired incremental longitudinal movement of the upper jaw applicator 20 and the lower jaw applicator 22 relative to each other.

Each tooth 92 has a base end 100 and a free end 102, and is tapered towards its free end 102. The teeth 92 are aligned along a longitudinal edge 104 of the rack of teeth 90 such that their base ends 100 are positioned along the longitudinal edge 104, with their free ends 102 pointing away from the longitudinal edge 104. In other words, a longitudinal axis 106 of each tooth 92 is perpendicular to a longitudinal axis 108 of the rack 90. The longitudinal axis 108 of the rack of teeth 90 is slightly offset from a longitudinal axis 110 of the lateral sides 16, 18 of the intra-oral device 10.

Turning now to the dowel 94, which is best seen in FIGS. 7 to 9, and 11 and 12, the dowel member 96 has a tapered configuration and is sized and shaped to be received in at least one of the spaces between the teeth 92 of the rack. The dowel member is arranged to inter-engage with the space between two teeth such that the dowel member is received in the space with the dowel free end at or near the longitudinal edge of the rack of teeth 90. The dowel adjustment arm 98 is spaced from the dowel member 96 by a neck 112 and has a longitudinal axis 114 parallel to a longitudinal axis 116 of the dowel member 96.

The dowel 94 is associated with the upper jaw applicator 20 and is mounted to the upper jaw applicator 20 by a resilient biasing mechanism 118 such that it is biased towards the locked position in which it is maintained in one of the spaces between the teeth 92. In the illustrated embodiments, the resilient biasing mechanism 118 is a spring 118. Other mechanisms are also possible for providing resilient bias towards the locked position. The locking mechanism 88 can be said to comprise the spring 118, or any other biasing means for providing a resilient bias to the dowel 94 towards the longitudinal edge 104 of the rack of teeth 90.

An opening 120 is provided in the upper jaw applicator 20, both in the upper left component 34 and the upper right component 36, for housing the resilient biasing mechanism 118 and at least a portion of the dowel 94. When assembled, at least a portion of the dowel adjustment arm 98 extends from the upper jaw applicator 20.

In use, to adjust the relative longitudinal position of the upper jaw applicator 20 and the lower jaw applicator 22, the dowel 94 is brought to the release position by applying force to the dowel adjustment arm 98 to push against the resilient bias mechanism 118. This causes the dowel member 96 to release from the locked position in the teeth 92. The dowel member 96 can then be moved to another position in the rack of teeth 90. Longitudinal adjustment of the upper and lower jaw applicators 20, 22 can thus be achieved by appropriate positioning of the dowel member 96 in the rack of teeth 90. Different configurations of the upper jaw applicator 20 and the lower jaw applicator 22 can thus be obtained, such as the upper jaw applicator 20 jutting more anteriorly than the lower jaw applicator 22, or the lower jaw applicator 22 jutting more anteriorly that the upper jaw applicator 20. The relative longitudinal positions between the upper jaw applicator 20 and the lower jaw applicator 22 are in the form of incremental steps, corresponding to the distance between the teeth 92.

In certain embodiments, a longitudinal adjustment between the upper and lower jaw applicators 20, 22 of up to about 13 mm can be obtained.

In use, one or both of the transverse adjustment mechanism 50 and the longitudinal adjustment mechanism 80 can be used to incrementally adjust a relative position between the upper jaw applicator 20 and the lower jaw applicator 22, and the left and right quadrants. For example, in certain types of pre-orthodontic treatment, the longitudinal adjustment using the longitudinal adjustment mechanism 80 is adjusted about once a month.

At least one guide 122 is provided between the upper face 62 of the lower jaw applicator 22 and the lower face 66 of the upper jaw applicator 20 for guiding the longitudinal movement in the longitudinal direction 26. The guide 122 also functions to restrict vertical movement (superior-anterior, in use) as well as transverse movement of the intra-oral device 10. Each guide comprises at least one guide rail 124 which can be slidingly received in an associated at least one guide slot 126 in an inter-engaging manner such that longitudinal movement between the upper and lower jaw applicators 20, 22 is permitted when the dowel 94 is in a released position.

In the illustrated embodiments, there is a guide 122 between the upper left component 34 and the lower left component 44 (i.e. the left quadrant), and also between the upper right component 36 and the lower right component 46 (i.e. the right quadrant). In this embodiment, each guide comprises a pair of guide rails 124 and corresponding guide slots 126. In other embodiments, each guide 122 may comprise any number of guide rails 124 and corresponding guide slots 126, or a plurality of guide rails 124 and corresponding guide slots 126. As can be seen, the guide rails 124 are provided on the lower components of the intra-oral device 10 (lower left component 44 and the lower right component 46), and the corresponding slots are provided on the upper components of the intra-oral device 10 (upper left component 34 and the upper right component 36). However, this could be reversed in other embodiments. The guide rails 214 are parallel to the longitudinal edge 104 of the rack of teeth 90. In certain embodiments, at least one of the guide rails 124 forms at least part of the longitudinal edge 104 of the rack of teeth 90. The guide rail 124 protrudes from the upper face 62 of the lower left component 44 and extends at least partially along the upper face 62. Similarly, the guide rail 124 protrudes from the upper face 62 of the lower right component 46 towards the lower face 66 of the upper right component 36. Each guide rail 124 has a base portion 128 and a top portion 130. The top portion 130 is wider than the base portion 128, which in some embodiments can serve to restrict vertical movement between the upper jaw applicator 20 and the lower jaw applicator 22. However, for the avoidance of doubt, and as described above, transverse movement between the left and right quadrants is permitted as per the transverse adjustment mechanism 50.

The intra-oral device 10 can be made of any biocompatible material. The material of the intra-oral device 10 may be a metal, a metal alloy, a ceramic, a polymer, or a rubber. In certain embodiments, the intra-oral device is made of a medical grade polymer or a medical grade rubber. The material of the intra-oral device 10 may be a polyethylene, such as a high molecular weight polyethylene or high density polyethylene, a polyurethane, or the like. The material may be substantially Bisphenol A free.

Figure 13:
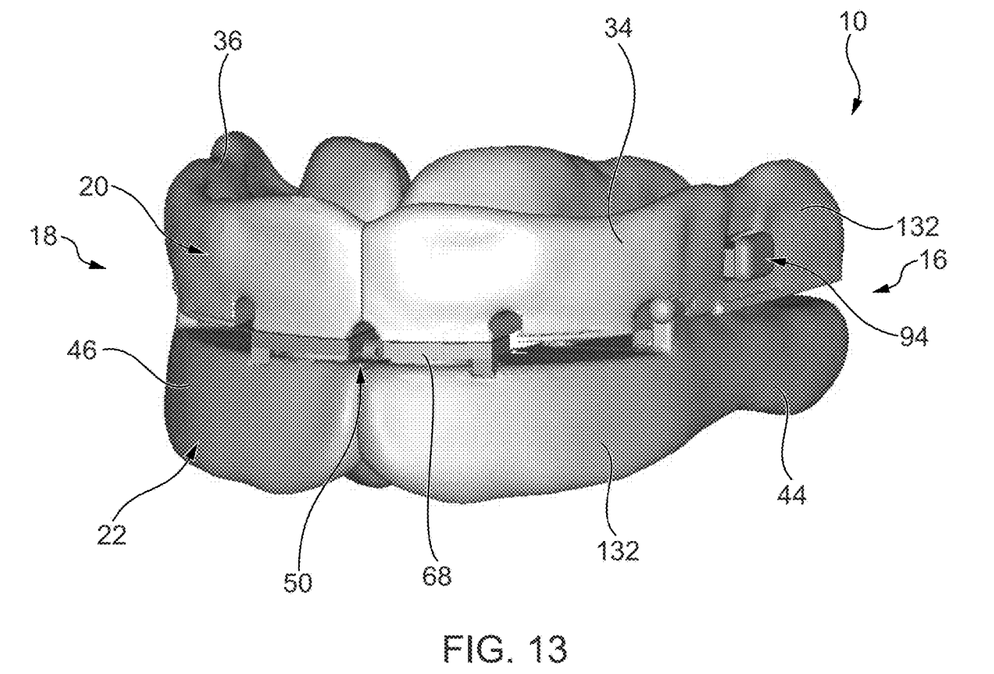
FIG. 13 is a perspective view of the intra-oral device of FIG. 1 and including a coating, according to certain embodiments of the technology.
Figure 14:
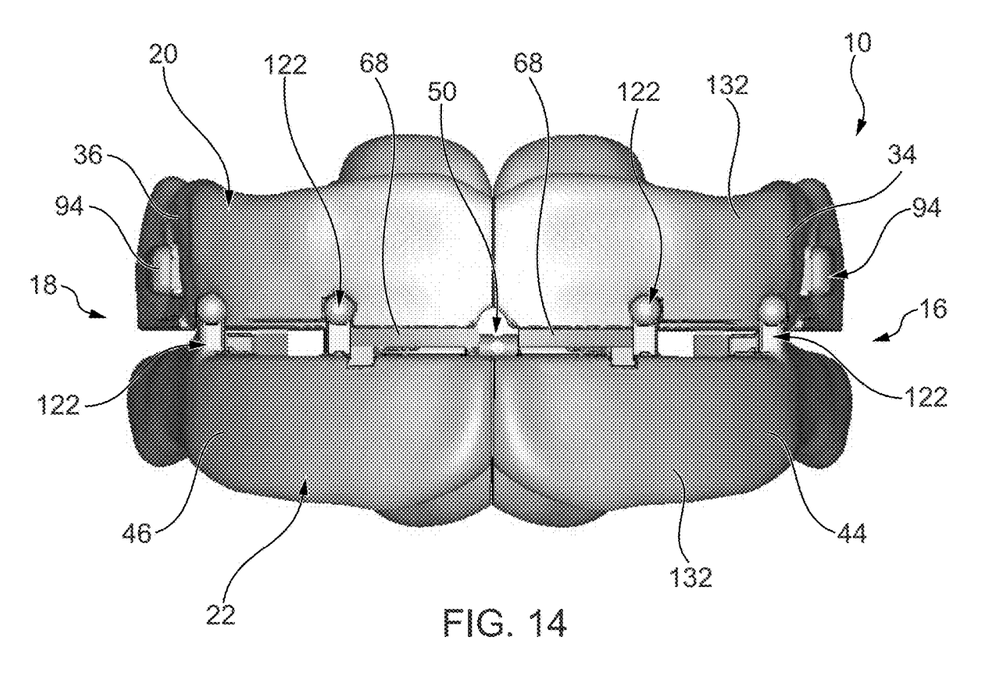
FIG. 14 is a front elevational view of the intra-oral device of FIG. 13.
Figure 15:
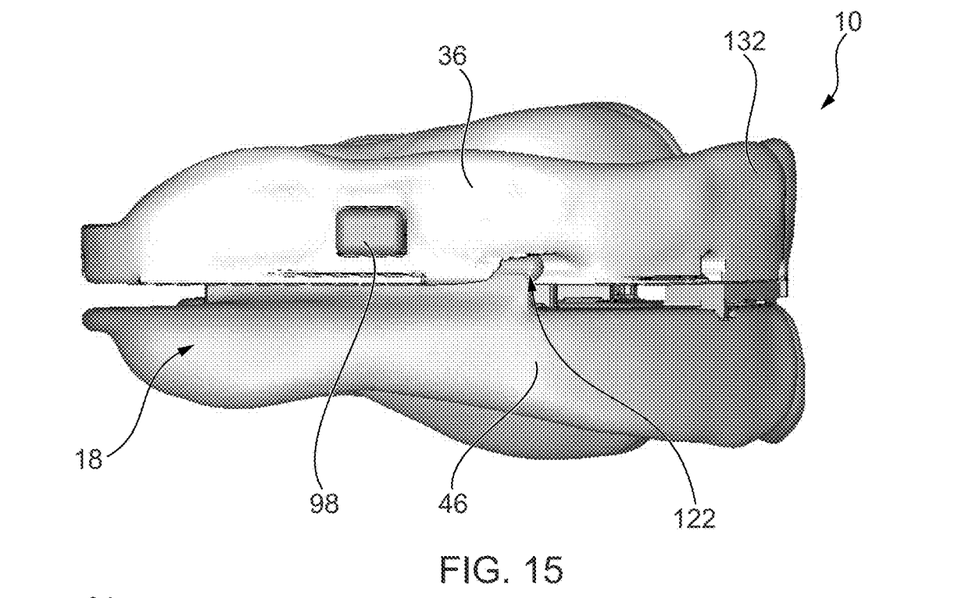
FIG. 15 is a right side view of the intra-oral device of FIG. 13.

As seen in FIGS. 1 to 9, the upper and lower jaw applicators 20, 22 have openings in their respective walls 30, 40 (i.e. a frame-like configuration). In this respect, in certain embodiments (FIGS. 13 to 15), the upper and lower jaw applicators 20, 22 are configured to be covered by a coating or covering 132 on at least a portion of the walls 30, 40 of the upper and lower jaw applicators 20, 22. The intra-oral device 10 shown in FIGS. 13 to 15 differs from the intra-oral device of FIGS. 1 to 12, in that it includes the covering 132. This can provide increased comfort to the user. As illustrated in FIGS. 13 to 15, the intra-oral device 10 includes the covering 132 on any surface of the intra-oral device 10 which can contact the user's gums, other soft tissues and/or teeth. The covering 132 may surround an outer surface of the walls 30, 40, and/or an inner surface of the walls 30, 40. Certain features of the intra-oral device 10 will not include the covering 132 such as the longitudinal adjustment mechanism 80, the transverse adjustment mechanism 50, the guides 122, and the slots 126.

In certain embodiments the covering 132 is surgical grade silicon which can be moulded to the user's teeth when warmed. Any other suitable coating is also possible. The coating can be a membrane. In the embodiments which include the coating 132, the upper and lower jaw applicators 20, 22 may have a frame-like structure as illustrated in FIGS. 1 to 15, or may have a solid configuration (i.e. no openings in the walls 30, 40).

Figure 16:
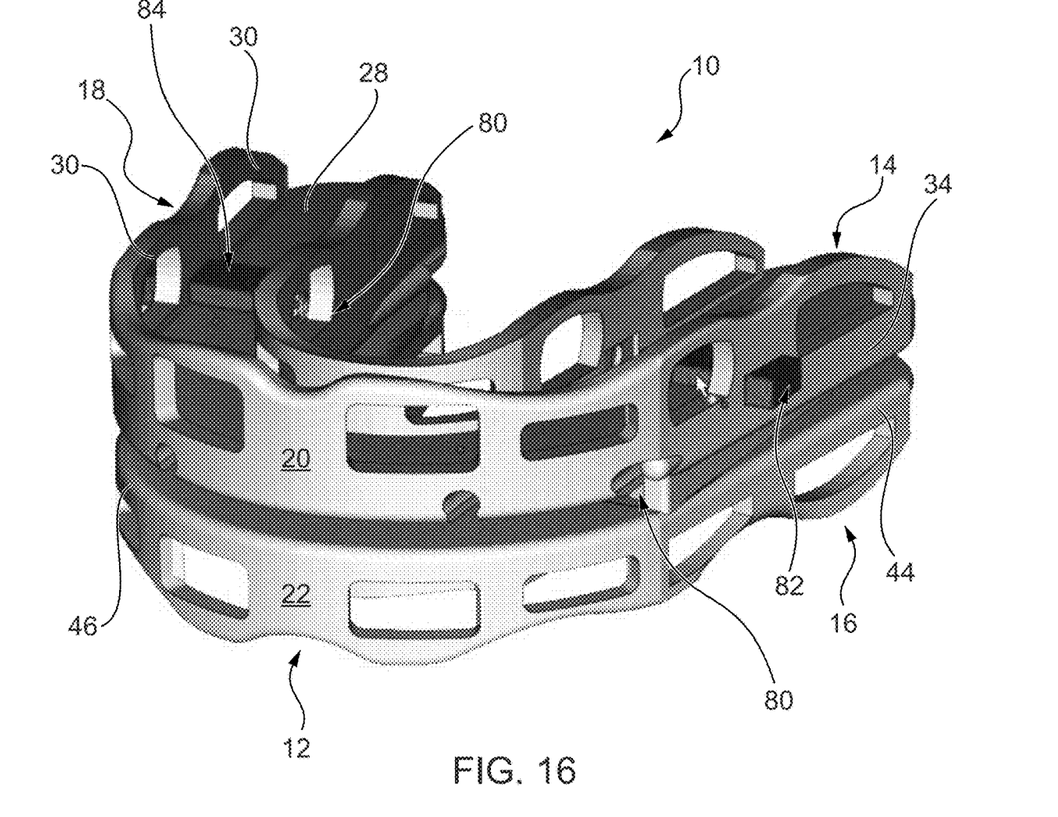
FIG. 16 is a perspective view of an intra-oral device according to certain other embodiments of the technology.

The intra-oral device 10 shown in FIG. 16 differs from that of FIGS. 1 to 15, in that the upper jaw applicator 20 is a single component (i.e. no upper left and right components 34, 36) and the lower jaw applicator 22 is a single component (i.e. no lower left and right components 44, 46). The longitudinal adjustment mechanism 80 is as shown and described in relation to FIGS. 1 to 15. There is no transverse adjustment mechanism 50. The intra-oral device of FIG. 16 may include a covering 132.

There is also provided an intra-oral device (not shown) which differs from that of FIGS. 1 to 15, in that the longitudinal adjustment mechanism 80 is omitted. The transverse adjustment mechanism 80 is as shown and described in relation to FIGS. 1 to 15.

From another aspect, there is provided a method of orthodontic treatment using embodiments of the intra-oral device 10 as described herein, in which one or both of a transverse adjustment mechanism 50, and a longitudinal adjustment mechanism 80 can be used to incrementally adjust a relative position between the upper jaw applicator 20 and the lower jaw applicator 22, and the left and right quadrants of the intra-oral device 10. For example, in one type of pre-orthodontic treatment, the longitudinal adjustment using the longitudinal adjustment mechanism is adjusted about once a month.

It should be expressly understood that not all technical effects mentioned herein need to be enjoyed in each and every embodiment of the present technology.

Modifications and improvements to the above-described implementations of the present technology may become apparent to those skilled in the art. For example, alternative transverse adjustment mechanisms and longitudinal adjustment mechanisms are possible. The foregoing description is intended to be exemplary rather than limiting. The scope of the present technology is therefore intended to be limited solely by the scope of the appended claims.

The invention claimed is:

1. An intra-oral device comprising:
an upper jaw applicator and a lower jaw applicator, the upper jaw applicator comprising an upper left component and an upper right component, and the lower jaw applicator comprising a lower left component and a lower right component;
lower threads on an upper face of the lower jaw applicator, and upper threads on a lower face of the upper jaw applicator, the upper threads extending across at least a portion of one or both of the upper left component and the upper right component, and the lower threads extending across at least a portion of one or both of the lower left component and lower right component;
a transverse adjustment mechanism for simultaneously adjusting a distance between:
the upper left component and the upper right component, and
the lower left component and the lower right component wherein the transverse adjustment mechanism comprises:
a threaded rod having two end portions, one end portion of the threaded rod being engageable with the upper left component and the lower left component, and the other end portion of the threaded rod engageable with the upper right component and the lower right component, wherein the threaded rod is engageable with the lower threads and the upper threads.

2. The intra-oral device of claim 1, further comprising an adjustment member for effecting rotation of the threaded rod about a longitudinal axis of the threaded rod, wherein the adjustment member comprises at least one opening positioned along the threaded rod, the at least one opening being engageable with a tool for effecting the rotation of the threaded rod.

3. The intra-oral device of claim 1, wherein the upper threads and the lower threads are each formed on a respective plate which is attached to the respective lower and upper faces of the upper jaw applicator and the lower jaw applicator, respectively.

4. The intra-oral device of claim 1, wherein one or both of the upper threads and the lower threads are formed directly in the respective lower and upper faces of the upper jaw applicator and the lower jaw applicator.

5. The intra-oral device of claim 1, further comprising:
a longitudinal adjustment mechanism for adjusting a relative longitudinal position of the upper jaw applicator to the lower jaw applicator.

6. The intra-oral device of claim 5, wherein the longitudinal adjustment mechanism comprises a linear ratchet mechanism on a longitudinal plane of the intra-oral device, the linear ratchet mechanism comprising:
a rack of teeth, the teeth being spaced along a longitudinal edge of the rack of teeth, and
a dowel having a dowel member arranged to inter-engage with the teeth of the rack of teeth.

7. The intra-oral device of claim 6, wherein the rack of teeth is associated with an upper face of the lower jaw applicator, and the dowel is associated with the upper jaw applicator.

8. The intra-oral device of claim 6, wherein the longitudinal adjustment mechanism further comprises a locking mechanism for maintaining the dowel in engagement with the teeth, the locking mechanism comprising a biasing member for providing a resilient bias to the dowel towards a base of the teeth along the longitudinal edge of the rack of teeth.

9. The intra-oral device of claim 1, further comprising a guide, associated with the upper jaw applicator and the lower jaw applicator, for guiding a longitudinal movement of the upper jaw applicator relative to the lower jaw applicator, the guide comprising at least one guide rail which can be slidingly received in an associated at least one guide slot.

10. The intra-oral device of claim 9, wherein the at least one guide rail is provided protruding from, and extending along at least a portion of, an upper face of the lower jaw applicator, and the associated the at least one guide slot is defined in a lower face of the upper jaw applicator.

11. The intra-oral device of claim 9, wherein the guide rail has a base portion and a top portion, the top portion being wider than the base portion.

12. The intra-oral device of claim 1, and including a silicon-based covering.

13. The intra-oral device of claim 1, wherein each of the upper jaw applicator and the lower jaw applicator comprise a base and walls defining a channel for receiving at least some teeth of a user in use.

14. An intra-oral device comprising an upper jaw applicator and a lower jaw applicator,
the upper jaw applicator comprising a base and walls defining a channel for receiving at least some upper teeth of a user in use, and configured as an upper left quadrant and an upper right quadrant;
the lower jaw applicator comprising a base and walls defining a channel for receiving at least some lower teeth of the user in use, and configured as a lower left quadrant and a lower right quadrant,
lower threads on an upper face of the lower jaw applicator and upper threads on a lower face of the upper jaw applicator, the upper threads extending across at least a portion of one or both of the upper left and upper right quadrants, and the lower threads extending across at least a portion of one or both of the lower left and lower right quadrants,
a transverse adjustment mechanism arranged to engage with each of the upper left quadrant, the upper right quadrant, the lower left quadrant and the lower right quadrant in order to simultaneously adjust a transverse distance between the upper right quadrant and the upper left quadrant, and between the lower right quadrant and the lower left quadrant, wherein the transverse adjustment mechanism comprises:
a threaded rod having two end portions, one end portion of the threaded rod being engageable with the upper left quadrant and the lower left quadrant, and the other end portion of the threaded rod engageable with the upper right quadrant and the lower right quadrant, wherein the threaded rod is engageable with the lower threads and the upper threads in use.

15. The intra-oral device of claim 14, further comprising an adjustment member for effecting rotation of the threaded rod about a longitudinal axis of the threaded rod, wherein the adjustment member comprises at least one opening positioned along the threaded rod, the at least one opening being engageable with a tool for effecting the rotation of the threaded rod.

16. The intra-oral device of claim 14, further comprising:
a longitudinal adjustment mechanism for adjusting a relative longitudinal position of the upper jaw applicator to the lower jaw applicator, wherein the longitudinal adjustment mechanism comprises a linear ratchet mechanism on a longitudinal plane of the intra-oral device, the linear ratchet mechanism comprising:
a rack of teeth, the teeth of the rack of teeth being spaced along a longitudinal edge of the rack of teeth, and
a dowel having a dowel member arranged to inter-engage with the teeth of the rack of teeth.

17. The intra-oral device of claim 16, wherein the longitudinal adjustment mechanism further comprises a locking mechanism for maintaining the dowel in engagement with the teeth of the rack of teeth, the locking mechanism comprising a biasing member for providing a resilient bias to the dowel towards a base of the teeth of the rack of teeth along the longitudinal edge of the rack of teeth.

* * * * *